United States Patent [19]

Hari et al.

[11] 4,138,568
[45] Feb. 6, 1979

[54] PROCESS FOR THE MANUFACTURE OF BENZIMIDAZOLONES-(2)

[75] Inventors: Stefan Hari, Allschwil; Ernesto Rinaldi, Reinach; Josef Somlo, Riehen, all of Switzerland

[73] Assignee: Ciba-Geigy Corporation, Ardsley, N.Y.

[21] Appl. No.: 801,941

[22] Filed: May 31, 1977

[30] Foreign Application Priority Data

Jun. 11, 1976 [CH] Switzerland ............... 7417/76

[51] Int. Cl.$^2$ ............................................. C07D 235/26
[52] U.S. Cl. .................................................. 548/305
[58] Field of Search ......................................... 548/305

[56] References Cited

U.S. PATENT DOCUMENTS

| 2,933,503 | 4/1960 | Clark et al. | 548/305 |
| 3,167,586 | 1/1965 | Smith | 260/563 |

FOREIGN PATENT DOCUMENTS

| 2052026 | 4/1972 | Fed. Rep. of Germany | 548/305 |
| 2131366 | 2/1973 | Fed. Rep. of Germany | 548/305 |
| 811692 | 4/1959 | United Kingdom | 548/305 |

OTHER PUBLICATIONS

Bottu, Chemical Abstracts, vol. 72 (1970), 66944d.
Clark et al., JACS, vol. 80 (1958), pp. 1657–1661.

*Primary Examiner*—Richard Raymond
*Attorney, Agent, or Firm*—Luther A. R. Hall

[57] ABSTRACT

Process for the manufacture of benzimidazolones-(2) wherein an o-phenylenediamine is reacted with optionally alkylated urea in the ratio of 1 to 1.3 moles per mole o-phenylenediamine in an organic solvent which has a solubility in water of not more than 5 g/l and has a boiling point above 100° C., at a temperature between 100° and 200° C.

6 Claims, No Drawings

PROCESS FOR THE MANUFACTURE OF BENZIMIDAZOLONES-(2)

The present invention provides a novel process for the manufacture of benzimidazolones-(2) which consists in reacting an o-phenylenediamine with optionally alkylated urea in a water-immiscible organic solvent.

It is known that benzimidazolone-(2) can be obtained by reacting o-phenylene-diamine with urea in water or in water-miscible solvents (cf. German Offenlegungsschrift No. 2,052,026 and French Pat. No. 1,561,830). Aside from the ecological problems, in consequence of the new regulations on effluent purification, this process has a number of further disadvantages. The reaction must be carried out in an autoclave under pressure; the foam which forms during the reaction clogs the pipes of the autoclave; the processes are not generally applicable and, in particular, do not make it possible to manufacture nitrobenzimidazolones-(2) and, in addition, require an at least 100% excess of urea. Two further processes for obtaining benzimidazolones from o-phenylenediamine are known from J. Amer.Chem. Soc. 80, 1657 (1958): the first by reaction with phosgene, the second by reaction with urea in the melt. In the reaction with phosgene, the formation of hydrochloric acid results in corrosion of the reactor. Moreover, the process using phosgene requires special savety measures on account of its toxic character. Difficulties in stirring and in discharging the reaction product occur during the reaction with urea in the melt. In addition, biuret always forms during the reaction. At the high reaction temperature this product sublimes and clogs the boiler in- and outlets.

It has now been found that all the above disadvantages are eliminated and benzimidazolones-(2) obtained in good yield by reacting an o-phenylenediamine with optionally alkylated urea in the ratio of 1 to 1.3 moles per mole of o-phenylenediamine in an organic solvent which has a solubility in water of not more than 5 g/l and a boiling point higher than 100° C., at a temperature between 100° and 200° C.

The o-phenylenediamines used as starting materials can be substituted, for example in the amino group, by an alkyl or aryl group and/or in the benzene nucleus by halogen atoms, alkyl, alkoxy, alkylsulphonyl, aryl, dialkylamino, acylamino, carboxylic acid, carboxylic acid ester, carbamoyl and substituted carbamoyl groups, alkylcarbamoyl and arylcarbonyl groups, hydroxyl, cyano and nitro groups.

Particularly interesting o-phenylenediamines for the process of the present invention are those of the formula

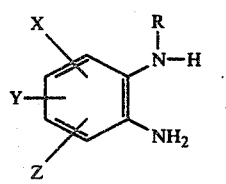

wherein
R represents a hydrogen atom, an alkyl group of 1 to 6 carbon atoms or a phenyl group which is unsubstituted or substituted by a chlorine or bromine atom, an alkyl or alkoxy group of 1 to 4 carbon atoms,
X represents a hydrogen atom, a chlorine or bromine atom, an alkyl, alkoxy or alkylsulphonyl group of 1 to 6 carbon atoms, a phenyl group which is unsubstituted or substituted by a chlorine or bromine atom, an alkyl or alkoxy group of 1 to 4 carbon atoms, or represents a dimethylamino, acetylamino or benzoylamino group, a carboxylic acid, methylcarbonyl, phenylcarbonyl, methoxycarbonyl, carbamoyl, methylcarbamoyl or phenylcarbamoyl group, a hydroxyl, cyano or nitro group, and
each of Y and Z independently represents a hydrogen, chlorine or bromine atom, an alkyl or alkoxy group of 1 to 6 carbon atoms.

Particularly preferred benzimidazolones-(2) are obtained by using as starting material an o-phenylenediamine of the formula

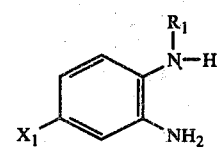

wherein
$R_1$ represents a hydrogen atom, a methyl or phenyl group, and
$X_1$ represents a hydrogen atom or, in particular, a nitro group.

An alkyl or alkoxy group represented by R, X, Y and Z is for example the methyl, ethyl, n-propyl, tert.-butyl, methoxy, ethoxy, n-butoxy or tert.-butoxy group.

A phenyl group represented by R and X is for example the o-, m- or p-chlorophenyl group, the o-, m- or p-tolyl group, the o-, m- or p-methoxyphenyl group, the o-, m- or p-ethoxyphenyl group, or the p-tert.-butoxyphenyl group.

An alkylsulphonyl group represented by X is in particular a methylsulphonyl or ethylsulphonyl group.

Examples of o-phenylenediamines suitable for obtaining the benzimidazolones-(2) of the present invention are:
o-phenylenediamine
3-chloro-1,2-phenylenediamine
4-chloro-1,2-phenylenediamine
4-bromo-1,2-phenylenediamine
3-methyl-1,2-phenylendiamine
4-methyl-1,2-phenylenediamine
4-ethyl-1,2-phenylenediamine
5-n-propyl-1,2-phenylenediamine
4-tert.-butyl-1,2-phenylenediamine
4-methoxy-1,2-phenylenediamine
5-ethoxy-1,2-phenylenediamine
5-methylsulphonyl-1,2-phenylenediamine
4-ethylsulphonyl-1,2-phenylenediamine
5-phenyl-1,2-phenylenediamine
5-p-tolyl-1,2-phenylenediamine
5-p-chlorophenyl-1,2-phenylenediamine
4-p-methoxyphenyl-1,2-phenylenediamine
4-p-ethoxyphenyl-1,2-phenylenediamine
5-p-tert.-butoxyphenyl-1,2-phenylenediamine
4-methylcarbamoyl-1,2-phenylenediamine
5-phenylcarbamoyl-1,2-phenylenediamine
4-dimethylamino-1,2-phenylenediamine
5-acetylamino-1,2-phenylenediamine
4-benzoylamino-1,2-phenylenediamine
4-methylcarbonyl-1,2-phenylenediamine
5-phenylcarbonyl-1,2-phenylenediamine
4-methoxycarbonyl-1,2-phenylenediamine 3,4-diamino-benzoic acid
5-hydroxy-1,2-phenylenediamine
4-cyano-1,2-phenylenediamine
4-nitro-1,2-phenylenediamine
4,5-dichloro-1,2-phenylenediamine
4,5-dibromo-1,2-phenylenediamine
4,6-dichloro-1,2-phenylenediamine
4-chloro-5-methyl-1,2-phenylenediamine
5-chloro-4-methyl-1,2-phenylenediamine
4,5-dimethyl-1,2-phenylenediamine
4,5-dimethoxy-1,2-phenylenediamine
4,5,6-trichloro-1,2-phenylenediamine
4,5,6-trimethyl-1,2-phenylenediamine
4-nitro-5-chloro-1,2-phenylenediamine
4-nitro-5-methyl-1,2-phenylenediamine
4-nitro-5-methoxy-1,2-phenylenediamine
4-nitro-5-ethyl-1,2-phenylenediamine
4-nitro-5-ethoxy-1,2-phenylenediamine
2-amino-4-nitro-$N_1$-methylaniline
2-amino-4-chloro-$N_1$-methylaniline
2-amino-4-methyl-$N_1$-methylaniline
2-amino-4-methoxy-$N_1$-methylaniline
2-amino-4-p-phenyl-$N_1$-methylaniline
2-amino-4-nitro-$N_1$-phenylaniline
2-amino-4-nitro-$N_1$-p-chlorophenylaniline
2-amino-4-nitro-5-chloro-$N_1$-methylaniline
2-amino-4-nitro-5-methyl-$N_1$-methylaniline
2-amino-4-nitro-5-methoxy-$N_1$-methylaniline
2-amino-4-nitro-5-ethyl-$N_1$-methylaniline The urea used for the cyclisation can also be N-mono- or N,N'-disubstituted by $C_1$–$C_4$-alkyl. As with urea, $N_1$- or $N_3$-unsubstituted benzimidazolones are then obtained in the cyclisation. The by-products consist of aliphatic amines. These reactions are of interest because they make it possible to observe the course of the cyclisation more exactly during the formation of the benzimidazolones. The following substituted ureas can be used for example:
N-methyl urea
N-ethyl urea
N,N'-dimethyl urea
N,N'-diethyl urea
N-methyl-N'-ethyl urea.

Preferably, however, unsubstituted urea is used.

As examples of organic solvents which are suitable for the process of the invention there may be mentioned:
chlorobenzene
o-dichlorobenzene
p-dichlorobenzene
dichlorobenzene (isomer mixture)
1,4,5-trichlorobenzene
1,2,4-trichlorobenzene
trichlorobenzene (isomer mixture)
nitrobenzene
toluene
o-xylene
m-xylene
p-xylene
xylene (isomer mixture)
bromobenzene
2-ethylbenzene
2-ethylhexanol
n-octanol
di-n-butyl ether
n-butyl acetate
1,1,2,2-tetrachloroethane
1,2,3-trichlorobenzene
tetrachloroethylene
decalin
n-amyl acetate p0 1,3-dichloropropane
2-nitrotoluene
4-nitrotoluene.

In the process of the invention, it is advantageous to use 1 to 2 moles of solvent referred to 1 mole of diamine.

The manufacture of the o-phenylenediamines and ureas to be used is known per se. The condensation of the o-phenylenediamine with urea in the organic solvent used according to the invention is effected at temperatures between 100° and 200° C., most advantageously however between 135° and 180° C.

The benzimidazolones-(2) obtained by the process of the invention, in particular the nitrobenzimidazoles-(2), are useful intermediates for the manufacture of pigments and dyes. They are used for this purpose by methods which are known per se.

The invention is illustrated by the following Examples, in which the parts and percentages are by weight unless otherwise indicated.

EXAMPLE 1

33.5 Parts of 2-amino-4-nitro-$N_1$-methylaniline and 15 parts of urea are heated in 100 parts by volume of o-dichlorobenzene for 3 hours to 172° C. Ammonia evolves from 100° C. The suspension is stirred for a further 2 hours at 172° C., then cooled to room temperature and filtered by suction. The filter cake is washed with a small amount of ethanol and suspended in a laboratory mixer with 200 parts by volume of 50% ethanol. After suction filtration and drying in vacuo at 60° C., 36.8 parts (95% of theory) of a light beige-coloured powder are obtained. The melting point of this product, 1-methyl-5-nitro-benzimidazoline-(2) of the formula

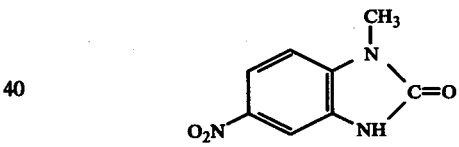

is between 302° and 303° C.

Analysis: Calculated: C 49.75; H 3.65; N 21.76%.
Found: C 49.5; H3.6; N 21.8%.

The following table lists further benzimidazolones-(2) of the formula

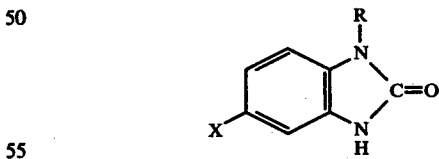

wherein the symbols X and R have the meanings given in columns 2 and 3 respectively. The solvent used in the condensation is indicated in column 4 and the yields and melting points of the products obtained are reported in the last two colums.

| Ex. | X | R | Solvent | Yield in % | Melting point in °C |
|---|---|---|---|---|---|
| 2 | H | H | chlorobenzene | 98 | 312–314 |
| 3 | H | H | o-dichlorobenezene | 98 | 313–315 |
| 4 | $NO_2$ | H | nitrobenzene | 95 | 298–299 |
| 5 | $CH_3$ | H | chlorobenezene | 97 | 293–295 |

-continued

| Ex. | X | R | Solvent | Yield in % | Melting point in °C |
|---|---|---|---|---|---|
| 6 | OCH$_3$ | H | chlorobenzene | 95 | 257-259 |
| 7 | Cl | H | o-dichlorobenzene | 95 | 323-324 |
| 8 | COOH | H | o-dichlorobenzene | 90 | Über 320 |
| 9 | NO$_2$ | C$_6$H$_5$CH$_2$ | o-dichlorobenzene | 86 | 239-240 |
| 10 | NO$_2$ | C$_6$H$_5$ | o-dichlorobenzene | 95 | 286-288 |

EXAMPLE 11

83.6 Parts of 2-amino-4-nitro-N-methylaniline and 37.5 parts of urea are stirred in 325 parts of o-dichlorobenzene. The reddish brown suspension is heated in the course of 1 ½ hours to 160° C. It becomes a solution at approx. 140° C. and simultaneously a fairly strong flow of ammonia evolves. The dark brown solution is stirred for 1 ½ hours at 160°-162° C. After 20 minutes a yellowish brown substance gradually precipitates from the solution and the evolution of ammonia slowly subsides. The fresh suspension is heated to 172° C. in the course of 12 minutes and stirred for 3 hours at this temperature. During this time, the evolution of ammonia comes to a complete halt. The yellowish brown suspension is finally cooled in an ice-water cooling bath to 18° C. in the course of 10 minutes, washed with 197 parts of ethanol in an Erlenmeyer flask, stirred for 10 minutes (magnetic stirrer) and filtered by suction. The filter cake (fine granules) is washed four times with 20 parts of ethanol, stirred for 3 minutes in a laboratory mixer with a solution of 197 parts of ethanol and 250 parts of wter and filtered by suction. The filter cake is washed with a solution of 10 parts of ethanol and 125 parts of water and dried in vacuo at 120° C., affording 91.6 parts (95% of theory) of 1-methyl-5-nitro-2-benzimidazolone.

The starting material, 2-amino-4-nitro-N-methylaniline, can be prepared as follows:

(a) 2,4-Dinitro-N-methylaniline 203.5 Parts of 99.5% 2,4-dinitrochlorobenzene are effectively stirred in 390 parts of water. The beige-coloured suspension is heated to 70° C in the course of 35 minutes, and at approx. 46° C. becomes a light brown emulsion. Then 120 parts by volume of a 41% aqueous solution of methylamine are added dropwise at 85° C. bath temperature in the course of half an hour. During the dropwise addition the temperature rises to 88° C. The emulsion solidifies slowly and a thick yellow crust forms on the wall of the flask. Thereafter 103 parts by volume of 30% sodium hydroxide solution are added dropwise in the course of a further hour. The temperature falls to below 81° C. The crust gradually detaches itself from the wall of the flask and a yellow suspension forms. This suspension is heated to 90° C. in the course of 15 minutes, stirred for 1 hour at 85° to 90° C., then cooled for 2 hours to 30° C. and filtered by suction. As the filter cake still contains some lumps, it is stirred in 305 parts of water in a laboratory mixer, filtered by suction, washed with 1150 parts of water and dried at 60° C. in vacuo, affording 193 parts of N-methyl-2,4-dinitro-aniline (97.8% of theory, referred to 2,4-dinitrochlorobenzene). The product has a melting point of 177°-178° C.

Analysis: Calculated: C42.65; H 3.58; N 21.32%. Found: C42.4; H 3.5; N 21.1%.

(b) 2-Amino-4-nitro-N-methylaniline

71 Parts of 2,4-dinitro-N-methylaniline and 53 parts of sodium hydrogen carbonate are stirred in 144 parts of methanol. The yellow suspension is heated in the course of 20 minutes to 40° C. Simultaneously, 81.9 parts of 60% sodium sulphide are dissolved in 144 parts of water of approx. 40° C. and 1.2 parts of 30% sodium hydroxide solution are added to the resultant solution. The turbid yellow solution is filtered. The clear yellow filtrate is added dropwise in the course of 2 hours to the suspension of 2,4-dinitro-N-methylaniline. An exothermic reaction occurs during the dropwise addition. The contents of the flask turn dark in colour. The new suspension is heated in the course of 1 hour to 70° C. and stirred for 15 minutes at this temperature (reflux). Then 144 parts of methanol are distilled off. The residue is cooled to 25° C. and 50 parts of ice are added. After suction filtration at 8° C., the filter cake is washed three times with 160 parts of water and dried in vacuo at 60° C. affording 56.8 parts of 2-amino-4-nitro-N-methylaniline (94.4% of theory). The melting point of the product is 177°-178° C.

Analysis: Calculated: C 50.29; H 5.43; N 25.14%. Found: C 50.0; H 5.4; N 25.0%.

EXAMPLE 12

216 Parts of o-phenylenediamine and 193.6 parts of N,N'-dimethyl urea are heated in 1000 parts of o-dichlorobenzene for 2 hours to 172° C. Methylamine evolves at 130° C. The suspension is stirred for a further 4 hours at 172° C., then cooled to room temperature and filtered by suction. The filter cake is washed with 800 parts by volume of ethanol and suspended in 1000 parts of water. This suspension is filtered by suction, washed with 100 parts of water and the filter cake is dried at 100° C., giving 250.8 parts (93.6% of theory) of benzimidazolone. The melting point of the product is between 312° and 315° C.

Analysis: Calculated: C 62.68; H 4.51; N 20.89%. Found: C 62.7; H 4.5; N 20.8%.

The benzimidazolones-(2) listed in the following table and having the formula

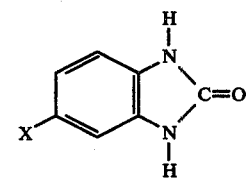

wherein X has the meaning given in column 2, can be obtained by the same process. The urea used in the condensation is listed in column 3. The yields obtained and the melting points of the products are reported in the last two columns of the table.

| Ex. | X | urea deriviative | yield in % | melting point in °C |
|---|---|---|---|---|
| 13 | H | N-methyl urea | 94.5 | 312-314 |
| 14 | NO$_2$ | N,N'-dimethyl urea | 85 | 298-299 |

EXAMPLE 15

Under the same conditions as in Example 1, 33.5 parts of 2-amino-6-nitro-N$_1$-methylaniline and 15 parts of urea are heated in 100 parts by volume of o-dichlorobenzene. The reaction product is worked up as in Example 1, giving 28.6 parts (74% of theory) of a light beige-coloured powder. The melting point of the resultant 1-methyl-7-nitro-2-benzimidazolone of the formula

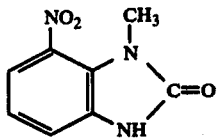

is between 270° and 272° C.

Analysis: Calculated: C 49.75; H 3.65; N 21.76%. Found: C49.6; H 3.7; N 21.8%.

We claim:

1. A process for the manufacture of nitrobenzimidazolones-(2) which comprises reacting an O-phenylenediamine of the formula

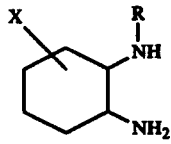

wherein
R represents a hydrogen atom, an alkyl group of 1 to 6 carbon atoms, phenyl or phenyl substituted by a chlorine atom, by a bromine atom, by an alkyl of 1 to 4 carbon atoms or by alkoxy of 1 to 4 carbon atoms, and X represents a nitro group,
with urea, N-alkylurea with alkyl of 1 to 4 carbon atoms or N,N'-dialkylurea with alkyl of 1 to 4 carbon atoms in the ratio of 1 to 1.3 moles of urea or alkylated urea per mole of O-phenylenediamine in a halogenated benzene organic solvent, which has a solubility in water of not more than 5 g/l and has a boiling point above 100° C., at a temperature between 100° and 200° C.

2. A process according to claim 1, wherein an unsubstituted urea is used as reactant.

3. A process according to claim 1, wherein a start is made from an o-phenylenediamine of the formula

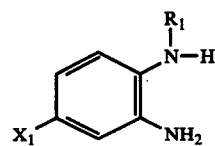

wherein $R_1$ represents a hydrogen atom, a methyl group or a phenyl group, and $X_1$ represents a nitro group.

4. A process according to claim 1, wherein 1 to 2 moles of solvent are used referred to 1 mole of diamine.

5. A process according to claim 4, wherein the halogenated benzene is chlorobenzene or o-dichlorobenzene.

6. A process according to claim 1, wherein the reaction is carried out at a temperature between 135° and 180° C.

* * * * *